United States Patent
Carr, Jr. et al.

(10) Patent No.: US 6,573,104 B2
(45) Date of Patent: Jun. 3, 2003

(54) DISPOSABLE CUP AND CONE USED IN BLOOD ANALYSIS INSTRUMENTATION

(75) Inventors: Marcus E. Carr, Jr., Midlothian, VA (US); Mark Licata, Doswell, VA (US)

(73) Assignee: Hemodyne, Incorporated, Richmond, VA (US)

( * ) Notice: Subject to any disclaimer, the term of this patent is extended or adjusted under 35 U.S.C. 154(b) by 0 days.

(21) Appl. No.: 09/852,149

(22) Filed: May 10, 2001

(65) Prior Publication Data

US 2002/0168294 A1 Nov. 14, 2002

(51) Int. Cl.[7] ................................................ G01N 33/86
(52) U.S. Cl. ............................ 436/69; 436/8; 422/73; 422/49
(58) Field of Search ........................ 422/68.1, 73, 99, 422/102; 436/8, 63, 69; 73/1.01, 1.02, 64.41, 790; 600/368, 369

(56) References Cited

U.S. PATENT DOCUMENTS

| | | | | |
|---|---|---|---|---|
| 4,986,964 A | * | 1/1991 | Carr et al. | 422/109 |
| 5,205,159 A | * | 4/1993 | Carr, Jr. | 422/73 |
| 5,293,772 A | * | 3/1994 | Carr, Jr. | 422/73 |
| 5,503,801 A | * | 4/1996 | Brugger | 210/436 |

FOREIGN PATENT DOCUMENTS

WO         01/12211     *   2/2001

* cited by examiner

*Primary Examiner*—Maureen M. Wallenhorst
(74) *Attorney, Agent, or Firm*—Whitham, Curtis & Christoffersn, PC

(57) ABSTRACT

Blood clot analysis instrumentation used to evaluate platelet function and clot structure by monitoring force development during clot retraction or upon application of a known amount of force can have a calibration check automatically performed by using a top member with a known amount of mass which is detachable from the instrumentation, and preferably is a disposable component. The calibration check is performed by monitoring force or displacement on a holding member with and without the top member attached. If the difference measured is within a preferred tolerance range, then the instrumentation can be deemed to be within the specifications deemed best suited for the instrument. The top member may also be modified to allow for mixing reagents with the clot, thereby avoiding the need to pre-mix blood with reagents before measurement. This can be accomplished by providing the top member with a rotation mechanism, such as an air driven fin assembly, that permits the top member to rotate forwards and/or backwards relative to the receptacle which holds the blood sample. The top member may also carry on board one or more reagents used for the diagnostic tests to be performed on the blood sample. Different top members might be used to perform different tests by being capable of dispensing different reagents. Moreover, a bar code or other indicia may be used to have the instrumentation automatically identify the test being performed, and this can also be used to provide information useful in regulating the mixing operation to be performed by the top member. Furthermore, a disposable liner may also be positionable within the receptacle such that the entire test can be performed with disposable components, thereby reducing clean up time, improving performance of the instrumentation, and enhancing the safety for the clinicians. Finally, the shape of the top and bottom members are configured in such a way as to have the evaporation force vector perpendicular to the clot retraction force vector.

30 Claims, 3 Drawing Sheets

DISPOSABLE CUP AND CONE USED IN BLOOD ANALYSIS INSTRUMENTATION

BACKGROUND OF INVENTION

1. Field of the Invention

The invention is directed to blood analysis instrumentation used to monitor force development or elastic modulus for a blood sample during clotting and dissolution.

2. Background Description

Blood analysis instrumentation used to analyze force development and elastic modulus of a blood sample during clotting and dissolution of a blood clot is described in detail in U.S. Pat. Nos. 4,986,964, 5,205,159, and 5,293,772 to Carr. The complete contents of these patents is herein incorporated by reference. As explained in the Carr patents, blood samples placed between a pair of spaced apart plates, one of which is connected to a transducer, can be evaluated for force development by measuring the pulling force caused by the blood clot. Force development is dependent on platelet function and arises from the internal actions of the platelets during clot retraction. Clot retraction is dependent on intact platelet membrane structure, normal platelet metabolic function, fibrin structure and normal platelet-fibrin interactions. Changes in clot retraction are sensitive to a spectrum of fluid phase and platelet abnormalities. If platelet function is abnormal or if platelets are absent, force development will be reduced or not occur. Measuring force development can be used in assessing risk of bleeding or thrombosis or a patient's propensity for stroke or other disorders. Clot dissolution can be identified as a decrease in elastic modulus. This can occur with the addition of dissolving agents such as tissue plasminogen activator (t-PA). Monitoring the effects of such dissolving agents on blood clots can assist in assessing the fibrinolytic potential of whole blood. Determination of elastic modulus assists physicians in assessing clot structure and is a measure of erythrocyte flexibility and general clot structure. As described in U.S. Pat. Nos. 5,205,159 and 5,293,772, by periodically applying a known amount of force to an upper plate, and by determining the deformation of the clot during clotting, the elastic modulus can be calculated.

SUMMARY OF INVENTION

It is an object of this invention to provide a disposable cone and cup for use in blood analysis instrumentation used to assess platelet function and clot structure. The disposable nature of the cone and cup provides benefits of safety and productivity because the clinicians are not required to clean patient blood samples from reusable plates.

It is another object of this invention to provide an automated calibration check method for use with blood analysis instrumentation used to assess platelet function and clot structure. By using a top member, e.g., a disposable cone, that is of a known mass and which is selectively detachable from a holding means that holds the top member a slight distance above the receptacle, the displacement or downward gravitation force on a transducer can be measured. A measurable difference will result when the top member is attached and when it is unattached. If this difference is within a specified tolerance, then the instrumentation can be deemed to be within the calibration specifications required for proper operation of the instrumentation.

It is yet another object of the invention to provide on-board mixing capabilities and on-board reagent delivery in blood analysis instrumentation. Automation of the instrumentation is highly desirable. Mixing reagents directly in the receptacle can enhance automation of instrumentation designed for analysis of platelet function and/or clot structure. By providing a mechanism to rotate the top member relative to the receptacle, mixing within the receptacle can be achieved. A preferred mechanism may include a plurality of fins which are driven by an air source; however, direct drive mechanisms might also be used. By providing a mechanism to deliver reagent directly in the receptacle, the need for a separate preparatory operation is avoided. In a preferred embodiment, the reagent is carried within the body of the top member, and is combined with the blood sample while in the receptacle.

According to the invention, the cone and cup are used as the top and bottom plates of the blood analysis instrumentation, and force development between these two members is monitored and used to assess the platelet function and clot structure. The conical shape allows for easy alignment of the cone and cup, and provides greater surface area to interact with the blood sample. Preferably, the cone and cup are disposable, thereby enhancing instrument cleanliness as well as productivity and safety for the clinicians. For example, for each test to be performed, the cup, which will preferably be in the form of a thin plastic liner (e.g., high density polyethylene, polyvinyl chloride, etc.), is inserted into a receptacle, and the cone shaped top member is positioned within the confines of the receptacle, but spaced slightly above the receptacle surfaces such that blood can engage the surfaces of both the receptacle (i.e., at the liner) and the top member (i.e., at the conical end). During clotting, the top member will be pulled by clot retraction forces toward the receptacle, and this force development is measured using a transducer that is preferably connected to the top member. Clot elastic modulus may also be measured by periodically applying a compression force to the top member and calculating the modulus based on the applied force and the deformation of the clot.

Using a top member of a known mass that is detachable from the blood analysis instrumentation permits an automated calibration check to be performed simply by comparing displacement or force measurements with and without the top member attached. In addition, the top member can be modified to allow for mixing the blood sample with reagents, and for carrying reagents on board which may be used for clot retraction and clot dissolution analysis. Bar coding permits different top members to be identified in an automated fashion (e.g., top members carrying different reagents, and which may require different mixing operations).

BRIEF DESCRIPTION OF DRAWINGS

The foregoing and other objects, aspects and advantages will be better understood from the following detailed description of the preferred embodiments of the invention with reference to the drawings, in which.

DETAILED DESCRIPTION OF THE PREFERRED EMBODIMENT OF THE INVENTION

Blood clot analysis instrumentation used to assess platelet function and clot structure are described in U.S. Pat. Nos. 4,986,964, 5,205,159, and 5,293,772. This invention is intended to be used in instrumentation similar to that described in those patents, and the complete contents of those patents are herein incorporated by reference.

Figure 1:
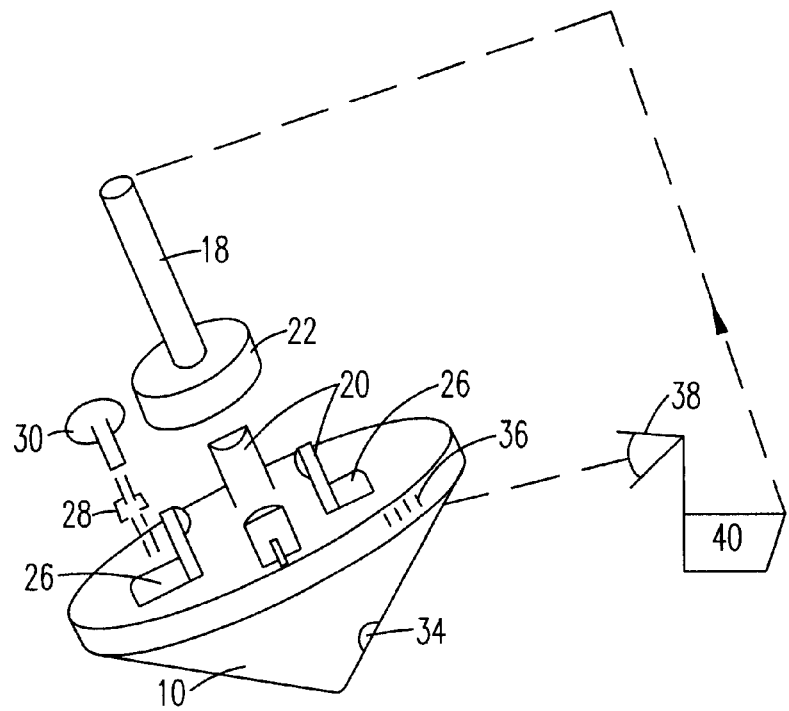
FIG. 1 is an isometric view of a top member according a preferred embodiment of this invention which is detachable from the holding member of the blood clot analysis instrumentation.
Figure 2:
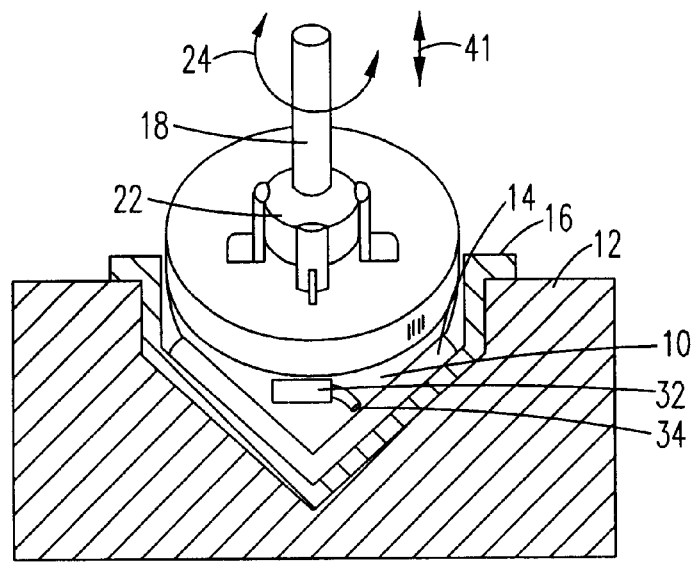
FIG. 2 is a view, partially in cross-section, which shows the top member of FIG. 1 being rotated while positioned in the receptacle of the blood clot analysis instrumentation.

FIG. 1 shows a top member 10 that is intended to function as a top plate of the blood clot analysis instrumentation. FIG. 2 shows the top member 10 positioned within receptacle 12 with a blood sample 14 therebetween. As described in the references incorporated above, the blood sample clots while positioned between top and bottom plates and exerts a pulling force which draws the top and bottom plates together. This pulling force, i.e., force development during clotting, is measured using a transducer connected to either or both the top or bottom plate. By making the top member 10 in a cone shape and the receptacle 12 in a conical cup shape, alignment of the top member 10 and receptacle 12 becomes very easy (i.e., simply align the point of the cone with the matching depression in the cup). Furthermore, the conical shape provides greater surface area for the blood sample 14 to engage on both the top member 10 and receptacle 12.

As is best shown in FIG. 2, it is preferable to use a plastic liner 16 within the receptacle 12. The plastic liner 16 can be any suitable material such as high density polyethylene or polyvinyl chloride. Similarly, the top member 10 is preferably made of plastic material. In operation, the plastic liner 16 would be placed in the receptacle 12 and secured thereto, then the blood sample 14 would be added, and then the top member 10 would be positioned in the receptacle. The top member 10 is held a distance above the base of the receptacle 12 such that the blood sample 12 can engage the surfaces of both components. In this way, force development exerted by platelets during clot contraction can be measured (e.g., by displacement of the top member 10 towards the receptacle 12). While not shown, the receptacle 12 can be cooled by coolant, peltier devices or other means to regulate the temperature of the blood sample 14 during analysis.

Figure 4A:
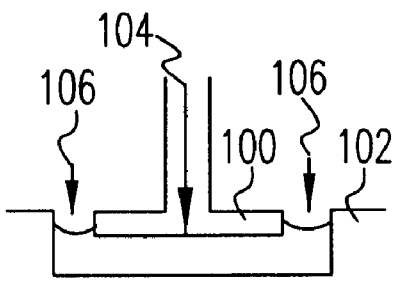
FIGS. 4a–b are schematic diagrams illustrating the platelet clot force development vector and the evaporative force vector for a flat top plate and cup.
Figure 4B:
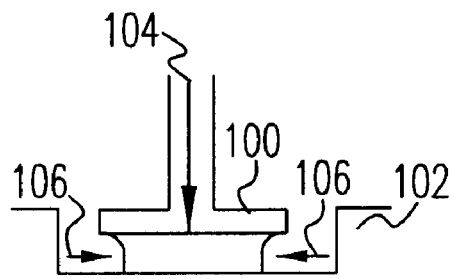
Figure 5A:
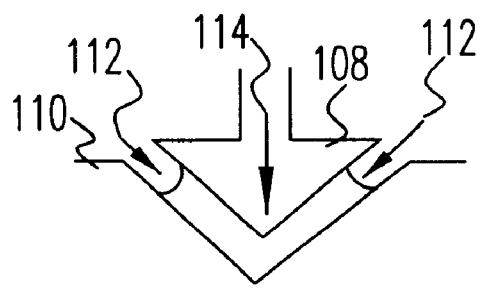
FIGS. 5a–b are schematic diagrams illustrating the platelet clot force development vector and the evaporative force vector for a conical top plate and cup.
Figure 5B:
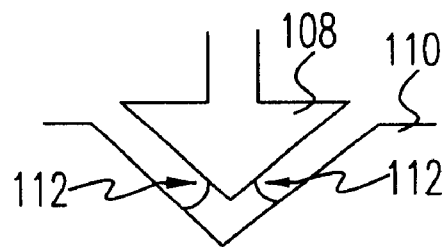
Figure 6A:
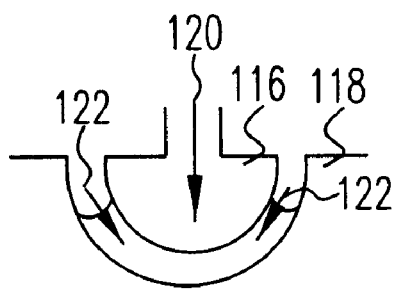
FIGS. 6a–b are schematic diagrams illustrating the platelet clot force development vector and the evaporative force vector for a half spherical top plate and cup.
Figure 6B:
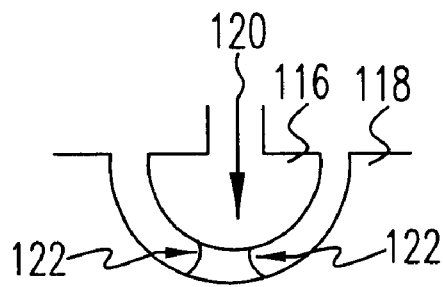

While FIGS. 1 and 2, show a conical shaped top member 10 and receptacle 12, virtually any shape that traps the entire sample between two surfaces in such a way as to move the evaporation force vector from parallel to the platelet contraction force vector towards perpendicular will be advantageous in the practice of this invention. For example, with reference to FIGS. 4a–b, it can be seen with a flat top plate 100 and cup 102, the platelet contractile force 104 and evaporative force 106 are initially parallel. However, as shown in FIGS. 5a–b, with a conical top plate 108 and cup 110, the evaporative force vector 112 is not parallel, but rather is oriented more towards perpendicular to the platelet clot retraction force vector 114. Likewise, as shown in FIGS. 6a–b, with a dome shaped top plate 116 and cup 118, the initial evaporative as force vector 120 is not parallel to the platelet clot force vector 122.

When the evaporative force vector is parallel to the platelet clot force vector, the effects of evaporation may be measured as part of the force signal. In some cases, without considering the evaporative force, inaccurate readings might result. This can be prevented by covering the exposed surface of the sample (the surfaces not between the top plate and bottom cup) with oil, or by placing the entire measurement instrumentation in a 100% humidity environment. However, by simply modifying the top plate and bottom cup shape, the change in evaporative force vector orientation may eliminate the need for using oil and humidified environments.

Most preferably, the liner 16 and top member 10 are disposable items. Thus, when a clinician or researcher performs a test on a blood sample, he or she simply places a liner in an opening in the receptacle, adds the sample of blood, connects the top member to the holding mechanism and begins measurement of force development. After use, the liner 16 and top member 10 can simply be thrown away. Having the liner 16 and top member 10 be disposable items enhances automation by limiting clean up requirements, protects the instrumentation from reagents or blood, and enhances safety by limiting the clinician's exposure to the blood sample.

An important feature of this invention is to have the top member 10 detachable from the holding means 18. In FIG. 1, the top member 10 is securable to the holding means 18 by a snap connection using connectors 20 that connect with bearing member 22. Other connections such as screw configurations, hooks, clips, etc., may also be used within the practice of this invention. The holding means 18 is shown simply as a tube or rod, but can take any form. The function of the holding means 18 is to hold the top member above the base of the receptacle, and to transmit contractile forces which are developed during clot retraction to a transducer.

The top member 10, according to another preferred embodiment of this invention, may function as a mixing device that allows mixing of reagents with the blood sample 14, while the blood sample is in the receptacle 12. As shown in FIG. 2 by arrow 24, the holding means 18 can be rotated about its axis in either one direction or opposite directions. This causes the blood sample 14 to mix with reagents placed in the receptacle due to the shear forces between the surfaces of the receptacle 12 and the top member 10. Rotation might be achieved using a direct drive or other mechanism. In a preferred embodiment, as shown in FIG. 1, the top member 10 has one or more fins 26 that extend upwardly. These fins are impinged by air 28, or other gases, from source 30. As shown in FIG. 2, the top member 10 then rotates freely about the holding means 18 on bearing 22.

Automation might also be improved by having the top member 10 carry one or more reagents used for blood analysis on-board within its body. As shown in FIG. 2, the reagents 32 can be housed within a compartment in the top member 10, and these reagents 32 can be dispensed into the receptacle 12 through a port 34 after the blood sample 14 is placed therein. In this way, the clinician avoids the requirement of adding reagents to the receptacle or combining the reagents with the blood sample prior to installation in the receptacle. The port 34 can simply be an opening that is taped over during storage and shipping of the top member 10, or could be a dissolvable member that provides access to the receptacle when it comes into contact with blood or reagents in the receptacle 12. Alternatively, the reagents 32 can also be housed inside the receptacle 12, instead of the top member 10, before their dispense. Further, the reagent 32 might also be dried on the surfaces of the top member 10 or receptacle 12.

A wide variety of reagents are employed in blood analysis, and depend on the test being performed in a standard test used to evaluate platelet function one might use thrombin, calcium, celite (silica), kaolin, collagen, and Russell Viper Venom. When using the blood analysis instrumentation as a surgical monitor, one might use heparinase I, [deamino-$Cys^1$,D-$Arg^8$]-vasopressin(DDAVP), protamine, atroxin, TAFI, tissue factor, t-PA, and reptilase as reagents. When assessing drug activity (i.e., using the instrumentation as a drug monitor), one might use TRAP, TRIP, platelet factor 4, Reopro, Integriln, and Agrostat. When using the blood analysis instrumentation as a fibrinolysis monitor, one might use tranexamic acid, aprotinin, streptokinase, urokinase, epsilon-amino caproic acid (EACA), and pro-urokinase. Having the reagents on board the top member 10 allows the clinician to perform the desired test without having to carefully add the reagents to the receptacle well with the blood sample 14, or requiring the clinician to carefully mix the reagents with the blood sample prior to installation of the blood sample in the receptacle 12. Furthermore, the clinician is not required to select the proper reagents for which ever test he or she desires since the top member 10 is provided pre-packaged with the reagents.

Blood analysis can be further automated by including indicia 36 such as a bar code on the top member. The indicia may be readable by a clinician, but are preferably read by an electronic eye or sensor 38. The indicia 36 could include such information as the reagent mix on board, the lot number, or other information. If the sensor 38 is positioned on the blood analysis instrumentation, and is connected to a computer 40, the bar code 36 could be used to identify the test being performed, and the computer could use this information to drive the mixing process or other operations of the instrumentation. Conceivably, several blood samples could be analyzed in an automated fashion by placing the samples in respective liners 16, feeding the liners to the receptacle 12, picking out suitable top members 10 with the reagents of interest using the sensor 38 to perform a test, and recording the results. The entire process could avoid unnecessary involvement of the clinician.

While not discussed in detail, the holding means 18 could be intermittently driven downward toward the bottom of the receptacle as indicated by arrow 41. As discussed in the incorporated Carr references, this function can be used to evaluate clot elastic modulus.

Figure 3A:
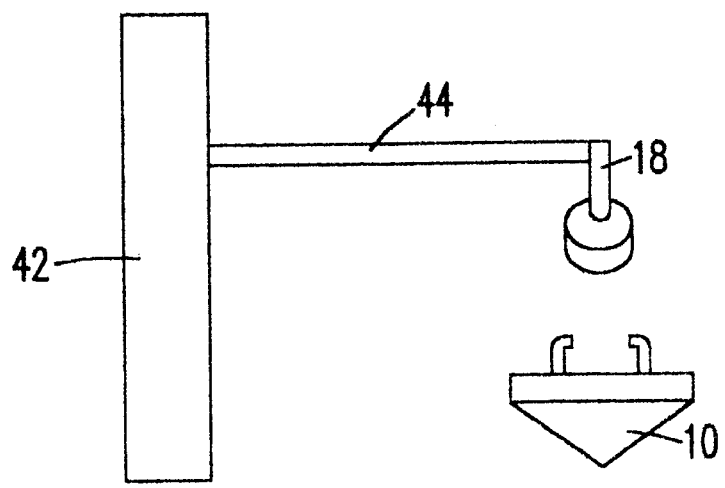
FIGS. 3a and 3b are cross-sectional view of the top member disengaged and engaged, respectively, from the holding member, whereby the top member is used as a calibration check.
Figure 3B:
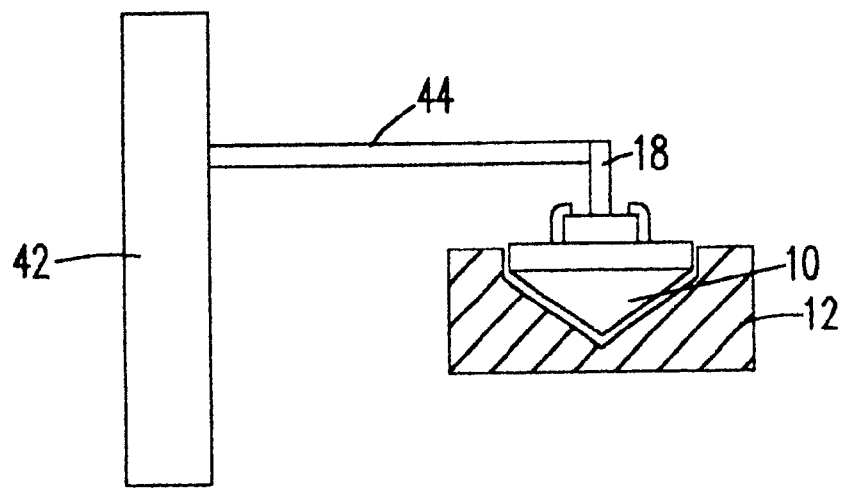

With reference to FIGS. 3a and 3b, the top member 10 can also be used as a calibration check for the blood analysis instrumentation. Specifically, when the top member 10 is not connected to the transducer 42 by arm 44 or other means, it will yield a value x which will reflect only the gravitational force of the holding means 18. When the top member 10 is connected to the transducer 42, it will yield a value x1" which will reflect the gravitational force of both the holding means 18 and the top member 10. If the mass of top member 10 is precisely known, then difference in measured values x–x1", provides a value that can be used as a calibration check (i.e., the value should be representative of the mass of the top member). If this difference value is within a prescribed tolerance (e.g., the difference value is near the value expected for the known mass of top member 10), then it can be inferred that the blood analysis instrumentation is within calibration parameters for the instrumentation.

The transducer 42 can measure a variety of parameters which are dependent upon the mass of the top member 10. For example, the transducer 42 could measure the strain of the downward gravitation force, or, more preferably, could measure the displacement of the top member downward due to its mass.

This calibration check should be understood to be a checking of the calibration of the instrument, not a calibration itself. If the difference value is not within a prescribed tolerance, the clinician, researcher, or service technician will know to adjust the blood analysis instrumentation using calibration weights, applied forces, or by other means, as is discussed in the above-identified Carr patents. The advantage of the calibration check method is that the clinician can determine whether the instrumentation is properly calibrated each time he or she performs a test on a blood sample.

While the invention has been described in terms of its preferred embodiments, the invention can be practiced with modification and variation within the spirit and scope of the appended claims.

What is claimed is:

1. A method for performing a calibration check for blood clot analysis instrumentation for monitoring force development, comprising the steps of:

performing a first measuring of a weight of a coupling arm and connector;

connecting a top member to said connector that is used in conjunction with a blood receptacle during monitoring of force development and elastic modulus, said top member having a prescribed mass;

performing a second measuring of a weight of said coupling arm, said connector, and said top member;

determining a mass of said top member as a difference between said first measurement and said second measurement; and comparing said difference to a predetermined tolerance, whereby said blood clot analysis instrumentation is in proper calibration if said difference is within said predetermined tolerance.

2. The method of claim 1 wherein said first measurement and said second measurement are displacement measurements and are measured with a displacement transducer.

3. The method of claim 1 wherein said first measurement and said second measurement are force measurements and are measured with a strain gauge.

4. A top member with a predetermined mass for use in blood clot analysis instrumentation for monitoring force development, comprising:

a body;

a blood contacting portion, extending from one end of said body and sized to fit within a receptacle of said blood clot analysis instrumentation, wherein said blood contacting portion is configured to move an initial evaporative force vector in said blood clot analysis instrumentation to an orientation which is not parallel to a platelet clot retraction force vector; and a connector extending from another end of said body, said connector selectively permitting attachment and removal from said blood clot analysis instrumentation.

5. The top member of claim 4 wherein said connector is a snap connection.

6. The top member of claim 4 further comprising a plurality of fins extending from said another end of said body, said plurality of fins being positioned about a periphery of said connector.

7. The top member of claim 4 further comprising at least one reagent positioned within said body.

8. The top member of claim 4 wherein the blood contacting portion has a conical shape.

9. The top member of claim 4 wherein the blood contacting portion as a half-spherical shape.

10. A method for monitoring force development by blood clot analysis instrumentation, comprising steps of:

placing a blood sample in a respective liner;

feeding said liner to a receptacle;

selecting a top member containing blood analysis reagents therein, wherein said top member and receptacle are configured to move an initial evaporative force vector in said blood clot analysis instrumentation to an orientation which is not parallel to a platelet clot retraction force vector;

positioning said top member within the receptacle with the blood sample, therebetween; and measuring a pulling force, exerted by the blood sample upon clotting.

11. The method of claim 10 wherein said top member, has a preset mass, and is used as a calibration check to determine if said blood analysis instrumentation is within a predetermined tolerance.

12. The method of claim 10, wherein said top member is rotated relative to said receptacle to mix said reagents with said blood sample.

13. The method of claim 10, wherein said blood analysis reagents in the top member are dispensed from said top member to the blood sample in the receptacle.

14. Blood clot analysis instrumentation for monitoring force development, comprising:

a receptacle for holding a blood sample;

a top member having at least a portion sized to fit within said receptacle, and configured to move an initial evaporative force vector in said blood clot analysis instrumentation to an orientation which is not parallel to a platelet clot retraction force vector;

means for holding said top member above said receptacle at a distance which allows said blood sample to engage surfaces of both said receptacle and said top member and pull them towards each other during clotting of said blood sample;

means for measuring a clot retraction force exerted by said blood sample during clotting; and means for connecting and disconnecting said top member from said means for holding said top member.

15. The blood clot analysis instrumentation of claim 14 wherein said top member has a preselected mass, and wherein said means for measuring clot retraction force also is used to perform a calibration check.

16. The blood clot analysis instrumentation of claim 14 further comprising at least one reagent positioned within said top member, and means for selectively releasing said at least one reagent from said top member into said receptacle.

17. The blood clot analysis instrumentation of claim 16 further comprising indicia on a surface of said top member which identifies said at least one reagent.

18. The blood clot analysis instrumentation of claim 17 wherein said indicia is a bar code.

19. The blood clot analysis instrumentation of claim 18 further comprising a bar code reader, and a computer, said computer adjusting said means for holding based on information identified by said bar code.

20. The blood clot analysis instrumentation of claim 17 wherein said indicia identifies a lot number of said at least one reagent.

21. The blood clot analysis instrumentation of claim 16 further comprising additional agents stored within said top member.

22. The blood clot analysis instrumentation of claim 16 further comprising a means for rotating said top member relative to said receptacle.

23. The blood clot analysis instrumentation of claim 22 further comprising a computer, and a means for inputting an identity of said at least one reagent into said computer, said computer operating said means for rotating under prescribed conditions based on said at least one reagent within said top member.

24. The blood clot analysis instrumentation of claim 14 further comprising a means for rotating said top member relative to said receptacle.

25. The blood clot analysis instrumentation of claim 24 wherein said means for rotating rotates said top member in at least two different directions.

26. The blood clot analysis instrumentation of claim 24 wherein said means for holding includes a snap connector.

27. The blood clot analysis instrumentation of claim 26 wherein said means for holding further comprises a bearing surface member which rotates to a connecting arm, and wherein said means for rotating comprises one or more air fins extended upwardly opposite to the portion of the top member sized to fit within the receptacle, and an air source for driving air against said fins.

28. The blood clot analysis instrumentation of claim 14 wherein said receptacle includes a liner therein, wherein said liner is constructed from plastic.

29. The blood clot analysis instrumentation of claim 14 wherein said receptacle includes a half-spherical cavity, and wherein said portion of said top member sized to fit within said receptacle has a half spherical shape matched to said half-spherical cavity.

30. The blood clot analysis instrumentation of claim 29 wherein said receptacle further comprises sidewalls extending upward from said half-spherical cavity.

* * * * *